United States Patent
Aoki et al.

(10) Patent No.: US 10,774,037 B2
(45) Date of Patent: Sep. 15, 2020

(54) METHOD FOR PRODUCING ALPHA-AMINO ACID

(71) Applicant: SHOWA DENKO K.K., Tokyo (JP)

(72) Inventors: Takanori Aoki, Setagaya-ku (JP); Akira Shibuya, Kawasaki (JP); Takamitsu Kobayashi, Fujisawa (JP); Hideo Miyata, Yokohama (JP); Shinya Tsukamoto, Kawasaki (JP); Manabu Kuwajima, Yokohama (JP); Motoki Murai, Shibuya-ku (JP)

(73) Assignee: SHOWA DENKO K.K., Tokyo (JP)

( * ) Notice: Subject to any disclaimer, the term of this patent is extended or adjusted under 35 U.S.C. 154(b) by 0 days.

(21) Appl. No.: 16/320,686

(22) PCT Filed: Jul. 25, 2017

(86) PCT No.: PCT/JP2017/026911
§ 371 (c)(1),
(2) Date: Jan. 25, 2019

(87) PCT Pub. No.: WO2018/021338
PCT Pub. Date: Feb. 1, 2018

(65) Prior Publication Data
US 2019/0161434 A1    May 30, 2019

(30) Foreign Application Priority Data

Jul. 28, 2016  (JP) ................... 2016-148584

(51) Int. Cl.
| | | |
|---|---|---|
| C07C 227/18 | (2006.01) |
| C07C 323/58 | (2006.01) |
| C07C 229/08 | (2006.01) |
| C07C 319/12 | (2006.01) |
| B01J 23/745 | (2006.01) |
| B01J 23/10 | (2006.01) |
| B01J 31/00 | (2006.01) |
| C07C 319/20 | (2006.01) |
| B01J 23/06 | (2006.01) |
| B01J 21/06 | (2006.01) |
| C07C 231/02 | (2006.01) |
| C07C 233/04 | (2006.01) |

(52) U.S. Cl.
CPC .......... *C07C 227/18* (2013.01); *B01J 21/066* (2013.01); *B01J 23/06* (2013.01); *B01J 23/10* (2013.01); *B01J 23/745* (2013.01); *B01J 31/00* (2013.01); *C07C 229/08* (2013.01); *C07C 231/02* (2013.01); *C07C 233/04* (2013.01); *C07C 319/12* (2013.01); *C07C 319/20* (2013.01); *C07C 323/58* (2013.01); *B01J 2523/10* (2013.01); *B01J 2523/27* (2013.01)

(58) Field of Classification Search
None
See application file for complete search history.

(56) References Cited

U.S. PATENT DOCUMENTS

2001/0037038 A1* 11/2001 Ponceblanc .......... C07C 319/20
562/559
2017/0275247 A1* 9/2017 Matsumura .......... C07C 321/14

FOREIGN PATENT DOCUMENTS

| JP | 3-093753 A | | 4/1991 | |
|---|---|---|---|---|
| JP | 3-093754 A | | 4/1991 | |
| JP | 3-093756 A | | 4/1991 | |
| JP | H0393754 | * | 4/1991 | |
| WO | WO-2016047516 A1 | * | 3/2016 | ............. C07B 61/00 |

OTHER PUBLICATIONS http://www.chem.ucalgary.ca/courses/351/Carey5th/Ch20/ch20-3-5-1.html, downloaded Jan. 16, 2020 (Year: 2020).*
https://en.wikipedia.org/wiki/Nitrile#Hydrolysis, downloaded Jan. 17, 2020 (Year: 2020).*
International Search Report for PCT/JP2017/026911 dated Oct. 17, 2017 [PCT/ISA/210].

* cited by examiner

*Primary Examiner* — Amy C Bonaparte
(74) *Attorney, Agent, or Firm* — Sughrue Mion, PLLC

(57) ABSTRACT

The present invention relates to a method for producing a specified α-amino acid, the method including allowing a specified α-amino acid amide and water to react with each other in the presence of a zirconium compound which contains zirconium and at least one metal element selected from the group consisting of lithium, nickel, copper, zinc, cesium, barium, hafnium, tantalum, cerium, and dysprosium.

12 Claims, No Drawings

METHOD FOR PRODUCING ALPHA-AMINO ACID

CROSS REFERENCE TO RELATED APPLICATIONS

This application is a National Stage of International Application No. PCT/JP2017/026911, filed on Jul. 25, 2017, which claims priority from Japanese Patent Application No. 2016-148584, filed on Jul. 28, 2016.

TECHNICAL FIELD

The present invention relates to a method for producing an α-amino acid.

BACKGROUND ART

Amino acids are compounds constituting a basic unit of protein, and an α-amino acid is an amino acid in which an amino group and a carboxy group are bonded to the same carbon. In general, the α-amino acid is frequently referred to simply as an amino acid.

The α-amino acid is in great demand for intermediates of a variety of industrial chemicals and also food additives, nutritional supplements, feed additives, medicaments, etc.

As its production method, in addition to a method of hydrolyzing a natural protein, a chemical synthesis method, a fermentation method, and an enzymatic method are adopted. Among these, as the chemical synthesis method, so-called hydantoin method and Strecker method, and so on are widely known.

The hydantoin method is a method in which an aldehyde or ketone compound is allowed to react with hydrogen cyanide and ammonium carbonate to synthesize hydantoin, which is then subjected to alkaline hydrolysis to obtain an α-amino acid. In the hydantoin method, in order to obtain an α-amino acid, after the alkaline hydrolysis, it is necessary to repeat a separation step of α-amino acid crystallized through neutralization with an acid, and a desalting step for removing a salt formed through neutralization is also needed, and thus, there was such a problem that the number of steps becomes large.

Meanwhile, the Strecker method is a method in which an aldehyde or ketone compound is allowed to react with hydrogen cyanide and ammonia to synthesize an α-aminonitrile, which is then hydrolyzed to obtain an α-amino acid. In the Strecker method, conventionally, the hydrolysis of the α-aminonitrile was also executed with an alkali, and similar to the aforementioned hydantoin method, neutralization with an acid was needed, and a desalting step for removing the thus formed salt was needed.

A technology for producing an α-amino acid capable of simplifying such complicated steps is demanded.

For example, PTL 1 describes a method for producing an α-amino acid, including bringing an α-amino acid amide into contact with water in a liquid phase in the presence of at least one metal oxide selected from the group consisting of zirconium oxide, titanium oxide, and niobium oxide, thereby performing hydrolysis.

In addition, PTL 2 describes a method for producing an α-amino acid, including bringing an α-amino acid amide into contact with water in a liquid phase in the presence of a complex metal oxide.

CITATION LIST

Patent Literature

PTL 1: JP 3-93753 A
PTL 2: JP 3-93754 A

SUMMARY OF INVENTION

Technical Problem

In PTL 1 or 2, it is mentioned that since zirconium oxide, titanium oxide, and niobium oxide, or the complex metal oxide has extremely high catalytic activity against the hydrolysis reaction of the α-amino acid amide, the α-amino acid can be obtained in a high yield from the α-amino acid amide under mild conditions, and the reaction and post-treatment can be carried out without using an alkali, and thus, the method is extremely economically advantageous as compared with the conventional method.

However, actually, in the case of using only zirconium oxide or titanium oxide as the catalyst, it is hardly said that the yield of the α-amino acid is industrially satisfactory. In addition, the complex metal oxide specifically disclosed in PTL 2 is limited to specified complex metal oxides, such as titanium oxide-zirconium oxide and titanium oxide-aluminum oxide. In the case of using such a catalyst, there is room for improvement from the viewpoint of improving the yield of the α-amino acid.

Under such circumstances, the present invention has been made, and an object thereof is to provide a method for producing an α-amino acid, which on synthesizing an α-amino acid from an α-amino acid amide, makes it possible to improve the yield of the α-amino acid.

Solution to Problem

In order to achieve the foregoing object, the present inventors made extensive and intensive investigations. As a result, it has been found that in hydrolysis of an α-amino acid amide, a specified zirconium compound exhibits high catalytic activity, and the aforementioned problem can be solved.

The present invention has been accomplished on the basis of such a finding.

Specifically, the present invention provides the following [1] to [8].

[1] A method for producing an α-amino acid represented by the following general formula (2), including allowing an α-amino acid amide represented by the following general formula (1) and water to react with each other in the presence of a zirconium compound which contains zirconium and at least one metal element selected from the group consisting of lithium, nickel, copper, zinc, cesium, barium, hafnium, tantalum, cerium, and dysprosium.

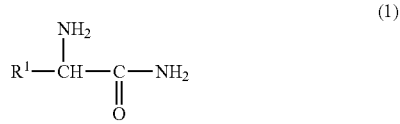

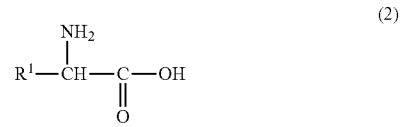

In the general formulae (1) and (2), $R^1$ is a hydrogen atom, an optionally substituted alkyl group having 1 to 6 carbon atoms, an optionally substituted cycloalkyl group having 3 to 6 carbon atoms, an optionally substituted aryl group having a ring-constituting carbon number of 6 to 10, or an optionally substituted heteroaryl group having a ring-constituting atom number of 4 to 13.

[2] The method for producing an α-amino acid as set forth in above [1], wherein the zirconium compound is a zirconium-containing oxide.

[3] The method for producing an α-amino acid as set forth in above [2], wherein the zirconium-containing oxide is a complex metal oxide containing zirconium and at least one metal element selected from the group consisting of lithium, nickel, copper, zinc, cesium, barium, hafnium, tantalum, cerium, and dysprosium.

[4] The method for producing an α-amino acid as set forth in above [2] or [3], wherein the zirconium-containing oxide is a supported type metal oxide in which a metal compound containing at least one metal element selected from the group consisting of lithium, nickel, copper, zinc, cesium, barium, hafnium, tantalum, cerium, and dysprosium is supported on zirconium oxide or the complex metal oxide.

[5] The method for producing an α-amino acid as set forth in above [3], wherein the content of the metal element other than zirconium in the complex metal oxide is 0.01 parts by mass or more and 100 parts by mass or less based on 100 parts by mass of zirconium.

[6] The method for producing an α-amino acid as set forth in above [4], wherein the supporting amount of the metal element other than zirconium in the supported type metal oxide is 0.01 parts by mass or more and 10.0 parts by mass or less based on 100 parts by mass of zirconium.

[7] The method for producing an α-amino acid as set forth in any of above [1] to [6], wherein the use amount of the zirconium compound is 1.0 part by mass or more and 200 parts by mass or less based on 100 parts by mass of the α-amino acid amide.

[8] The method for producing an α-amino acid as set forth in any of above [1] to [7], wherein the α-amino acid amide is glycine amide, alanine amide, or methionine amide.

Advantageous Effects of Invention

In accordance with the present invention, a method for producing an α-amino acid, which on synthesizing an α-amino acid from an α-amino acid amide, makes it possible to improve the yield of the α-amino acid can be provided.

DESCRIPTION OF EMBODIMENTS

Though the present invention is hereunder described in detail, it should be construed that the present invention is not limited to embodiments as mentioned later.

[Production Method of α-Amino Acid]

The production method of an α-amino acid of the present invention is a method for producing an α-amino acid represented by the following general formula (2), including allowing an α-amino acid amide represented by the following general formula (1) and water to react with each other in the presence of a zirconium compound which contains zirconium and at least one metal element selected from the group consisting of lithium, nickel, copper, zinc, cesium, barium, hafnium, tantalum, cerium, and dysprosium.

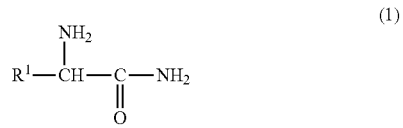

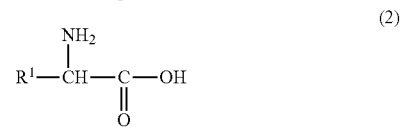

In the general formulae (1) and (2), $R^1$ is a hydrogen atom, an optionally substituted alkyl group having 1 to 6 carbon atoms, an optionally substituted cycloalkyl group having 3 to 6 carbon atoms, an optionally substituted aryl group having a ring-constituting carbon number of 6 to 10, or an optionally substituted heteroaryl group having a ring-constituting atom number of 4 to 13.

<α-Amino Acid Amide>

The α-amino acid amide is a compound represented by the following general formula (1).

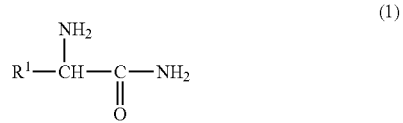

In the general formula (1), $R^1$ is a hydrogen atom, an optionally substituted alkyl group having 1 to 6 carbon atoms, an optionally substituted cycloalkyl group having 3 to 6 carbon atoms, an optionally substituted aryl group having a ring-constituting carbon number of 6 to 10, or an optionally substituted heteroaryl group having a ring-constituting atom number of 4 to 13.

It is to be noted that the carbon number, the ring-constituting carbon number, or the ring-constituting atom number do not include the carbon number and the atom number of a substituent.

The wording "optionally substituted" as referred to herein means that each of the aforementioned groups may have a substituent or may not have a substituent. For example, the optionally substituted alkyl group having 1 to 6 carbon atoms expresses a substituted alkyl group having 1 to 6 carbon atoms or an unsubstituted alkyl group having 1 to 6 carbon atoms.

$R^1$ is preferably a hydrogen atom or an optionally substituted alkyl group having 1 to 6 carbon atoms, and more preferably an optionally substituted alkyl group having 1 to 6 carbon atoms.

Examples of the alkyl group having 1 to 6 carbon atoms include a methyl group, an ethyl group, a n-propyl group, a n-butyl group, a n-pentyl group, a n-hexyl group, and structural isomers thereof (for example, an isopropyl group, an isobutyl group, a sec-butyl group, a tert-butyl group, etc.). The alkyl group having 1 to 6 carbon atoms is preferably an alkyl group having 1 to 4, more preferably an alkyl group having 1 to 3 carbon atoms, and still more preferably an alkyl group having 1 or 2 carbon atoms. The alkyl group having 1 or 2 carbon atoms is a methyl group or an ethyl group, respectively.

Examples of the cycloalkyl group having 3 to 6 carbon atoms include a cyclopropyl group, a cyclobutyl group, a cyclopentyl group, and a cyclohexyl group.

Examples of the aryl group having a ring-constituting carbon number of 6 to 10 include a phenyl group and a naphthyl group.

Examples of the heteroaryl group having a ring-constituting atom number of 4 to 13 include a pyrrolidinyl group, an imidazolyl group, and an indolyl group.

Examples of the substituent to be used in the "optionally substituted" case include at least one selected from the group consisting of a methyl group, an ethyl group, a hydroxy group, a carboxy group, a methoxy group, an amino group, a methylthio group, a mercapto group, a phenyl group, a hydroxyphenyl group, a benzyl group, an indolyl group, an imidazolyl group, a guanidino group, and a carbamoyl group.

Specifically, examples of the α-amino acid amide represented by the general formula (1) include at least one selected from the group consisting of glycine amide, alanine amide, methionine amide, isoleucine amide, leucine amide, lysine amide, cysteine amide, phenylalanine amide, tyrosine amide, threonine amide, tryptophan amide, valine amide, histidine amide, arginine amide, aspartic acid amide, asparagine amide, glutamic acid amide, glutamine amide, and serine amide. Among these α-amino acid amides, glycine amide, alanine amide, or methionine amide is preferred, and methionine amide is more preferred.

The amount of the α-amino acid amide which is used in the present invention is preferably 5.0% by mass or more, more preferably 7.5% by mass or more, still more preferably 9.0% by mass or more, and yet still more preferably 9.5% by mass or more based on 100% by mass of the total liquid amount of the reaction solution containing the α-amino acid amide and water from the viewpoint of improving the yield of the resulting α-amino acid; and it is preferably 50.0% by mass or less, and more preferably 40.0% by mass or less from the viewpoint of productivity, and still more preferably 30.0% by mass or less, yet still more preferably 20.0% by mass or less, even yet still more preferably 15.0% by mass or less, and even still more preferably 13.0% by mass or less from the viewpoint of improving the yield of the α-amino acid.

<α-Amino Acid>

The α-amino acid is a compound represented by the following general formula (2).

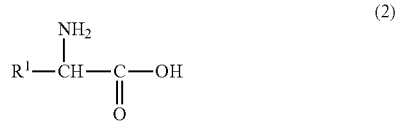

(2)

In the general formula (2), $R^1$ is the same as $R^1$ in the general formula (1), and preferred examples thereof are also the same.

Specifically, examples of the α-amino acid represented by the general formula (2) include at least one selected from the group consisting of glycine, alanine, methionine, isoleucine, leucine, lysine, cysteine, phenylalanine, tyrosine, threonine, tryptophan, valine, histidine, arginine, aspartic acid, asparagine, glutamic acid, glutamine, proline, and serine. Among these α-amino acids, glycine, alanine, or methionine is preferred, and methionine is more preferred.

<Zirconium Compound>

The zirconium compound contains zirconium and at least one metal element selected from the group consisting of lithium, nickel, copper, zinc, cesium, barium, hafnium, tantalum, cerium, and dysprosium. The zirconium compound acts as a catalyst in the reaction of hydrolyzing the α-amino acid amide to obtain the α-amino acid.

The zirconium compound is preferably a zirconium-containing oxide containing zirconium and at least one metal element selected from the group consisting of lithium, nickel, copper, zinc, cesium, barium, hafnium, tantalum, cerium, and dysprosium.

From the viewpoint of more improving the yield of the α-amino acid, the metal element other than zirconium is preferably at least one selected from the group consisting of lithium, nickel, copper, zinc, hafnium, tantalum, and dysprosium, and more preferably at least one selected from the group consisting of lithium, nickel, zinc, tantalum, and dysprosium.

The zirconium compound may be used either alone or in combination of two or more thereof.

The content of the metal element other than zirconium in the zirconium compound is preferably 0.01 parts by mass or more, more preferably 0.05 parts by mass or more, and still more preferably 0.1 parts by mass or more based on 100 parts by mass of zirconium from the viewpoint of improving the productivity; and it is preferably 100 parts by mass or less, more preferably 70.0 parts by mass or less, still more preferably 50.0 parts by mass or less, yet still more preferably 30.0 parts by mass or less, and even yet still more preferably 20.0 parts by mass or less from the viewpoint of inhibiting the side-reaction.

(Zirconium-Containing Oxide)

As for the zirconium-containing oxide, the zirconium-containing oxide is preferably a complex metal oxide containing zirconium and at least one metal element selected from the group consisting of lithium, nickel, copper, zinc, cesium, barium, hafnium, tantalum, cerium, and dysprosium (hereinafter also referred to as "zirconium-containing complex metal oxide").

[Zirconium-Containing Complex Metal Oxide]

In the case where the zirconium-containing oxide is the zirconium-containing complex metal oxide, from the viewpoint of more improving the yield of the α-amino acid, the metal element other than zirconium is preferably at least one selected from the group consisting of lithium, nickel, copper, zinc, hafnium, tantalum, and cerium.

The content of the metal element other than zirconium in the zirconium-containing complex metal oxide is preferably 0.01 parts by mass or more, more preferably 0.04 parts by mass or more, and still more preferably 0.1 parts by mass or more based on 100 parts by mass of zirconium from the viewpoint of improving the productivity; and it is preferably 100 parts by mass or less, more preferably 70.0 parts by mass or less, still more preferably 40.0 parts by mass or less, yet still more preferably 30.0 parts by mass or less, and even yet still more preferably 20.0 parts by mass or less from the viewpoint of inhibiting the side-reaction.

{Production Method of Zirconium-Containing Complex Metal Oxide}

As for the production method of the zirconium-containing complex metal oxide, the zirconium-containing complex metal oxide can be, for example, produced by a method described in the section of Examples as mentioned later (hydrothermal synthesis method), a coprecipitation method, or a sol-gel method.

For example, there is exemplified a method in which a feed raw material of zirconium, a feed raw material of other metal element than zirconium, and a solvent are mixed and heated to obtain the zirconium-containing complex metal oxide.

Examples of the feed raw material of zirconium include a salt of zirconium, such as an acetate, a carbonate, a nitrate, a sulfate, and an organic acid salt; a halide, such as a chloride, a bromide, and an iodide; a hydroxide; an alkoxide; and an oxyhalide. The feed raw material may be either an anhydride or a hydrate.

Examples of the feed raw material of other metal element than zirconium include a salt of the aforementioned at least one metal element selected from the group consisting of lithium, nickel, copper, zinc, cesium, barium, hafnium, tantalum, cerium, and dysprosium, such as an acetate, a carbonate, a nitrate, a sulfate, and an organic acid salt; a halide, such as a chloride, a bromide, and an iodide; a hydroxide; an alkoxide; and an oxyhalide. The feed raw material may be either an anhydride or a hydrate.

Examples of the solvent include water and/or a polar solvent other than water. As the polar solvent, one capable of dissolving the feed raw material of a metal element therein may be used, and examples thereof include an alcohol, such as methanol, ethanol, 1-propanol, 2-propanol, and 1-butanol.

Furthermore, ammonia, sodium hydroxide, hydrazine, hydrogen peroxide, sodium persulfate, a fatty acid, or the like may be mixed, as the need arises.

The mixing method of the feed raw material of zirconium, the feed raw material of other metal element than zirconium, and the solvent is not particularly limited and may be performed such that the mixture becomes uniform. Preferably, the feed raw material of zirconium and the feed raw material of other metal element than zirconium are mixed such that the resulting zirconium-containing complex metal oxide satisfies the aforementioned content of the metal element.

The blending amount of the feed raw material of other metal element than zirconium is preferably 1.0 part by mass or more, more preferably 1.5 parts by mass or more, still more preferably 2.0 parts by mass or more, and yet still more preferably 5.0 parts by mass or more, and it is preferably 100 parts by mass or less, more preferably 70.0 parts by mass or less, and still more preferably 40.0 parts by mass or less, as expressed in terms of the metal element other than zirconium based on 100 parts by mass of zirconium in the feed raw material of zirconium.

Thereafter, the resulting mixture is heated in the solvent. The temperature at the time of heating is preferably 100° C. or higher, more preferably 150° C. or higher, and still more preferably 200° C. or higher, and it is preferably 350° C. or lower, more preferably 320° C. or lower, and still more preferably 300° C. or lower. Though the heating time is not particularly limited, it is preferably 1 hour or more, more preferably 3 hours or more, and still more preferably 5 hours or more, and it is preferably 200 hours or less, more preferably 100 hours or less, and still more preferably 50 hours or less.

After heating, cooling to room temperature is performed, and the resulting mixture (solid) is washed, filtered, and then dried. The mixture (solid) obtained through these processes is then baked in air at a high temperature, whereby the zirconium-containing complex metal oxide can be obtained. Though the temperature at the time of baking is not particularly limited, it is preferably 300° C. or higher, more preferably 400° C. or higher, and still more preferably 450° C. or higher, and it is preferably 1,000° C. or lower, more preferably 900° C. or lower, and still more preferably 800° C. or lower. Though the baking time is not particularly limited, it is preferably 1 hour or more, more preferably 2 hours or more, and still more preferably 3 hours or more, and it is preferably 50 hours or less, more preferably 40 hours or less, and still more preferably 30 hours or less.

[Metal Supported Type Zirconium-Containing Oxide]

From the viewpoint of improving the productivity, preferably, the zirconium-containing oxide may be a supported type metal oxide in which a metal compound containing at least one metal element selected from the group consisting of lithium, nickel, copper, zinc, cesium, barium, hafnium, tantalum, cerium, and dysprosium is supported on zirconium oxide or the zirconium-containing complex metal oxide (hereinafter also referred to as "metal supported type zirconium-containing oxide").

The metal supported type zirconium-containing oxide is more preferably a supported type metal oxide in which a metal compound containing at least one metal element selected from the group consisting of lithium, nickel, copper, zinc, cesium, barium, hafnium, tantalum, cerium, and dysprosium is supported on the zirconium-containing complex metal oxide containing hafnium and zirconium or zirconium oxide; and still more preferably a supported type metal oxide in which a metal compound containing at least one metal element selected from the group consisting of lithium, nickel, copper, zinc, cesium, barium, hafnium, tantalum, cerium, and dysprosium is supported on the zirconium-containing complex metal oxide containing hafnium and zirconium.

In the case where the zirconium-containing oxide is the metal supported type zirconium-containing oxide, from the viewpoint of more improving the yield of the $\alpha$-amino acid, the metal element other than zirconium, which the metal compound to be supported on zirconium oxide or the zirconium-containing complex metal oxide contains, is preferably at least one selected from the group consisting of lithium, zinc, cesium, barium, and dysprosium, more preferably at least one selected from the group consisting of lithium, zinc, cesium, and dysprosium, and still more preferably at least one selected from the group consisting of lithium, zinc, and dysprosium.

The supporting amount of the metal element other than zirconium in the metal supported type zirconium-containing oxide is preferably 0.01 parts by mass or more, more preferably 0.05 parts by mass or more, still more preferably 0.1 parts by mass or more, yet still more preferably 0.5 parts by mass or more, and even yet still more preferably 0.7 parts by mass or more based on 100 parts by mass of zirconium from the viewpoint of improving the productivity; and it is preferably 10.0 parts by mass or less, more preferably 7.0 parts by mass or less, still more preferably 5.0 parts by mass or less, yet still more preferably 3.0 parts by mass or less, and even yet still more preferably 1.5 parts by mass or less from the viewpoint of inhibiting the side-reaction.

The content of the metal element other than zirconium in the metal supported type zirconium-containing oxide is preferably 0.1 parts by mass or more, more preferably 0.8 parts by mass or more, still more preferably 1.5 parts by mass or more, and yet still more preferably 1.7 parts by mass or more based on 100 parts by mass of zirconium from the viewpoint of improving the productivity; and it is preferably 10.0 parts by mass or less, more preferably 7.0 parts by mass or less, still more preferably 5.0 parts by mass or less, yet still more preferably 3.0 parts by mass or less, even yet still more preferably 2.5 parts by mass or less from the viewpoint of inhibiting the side-reaction.

The content of the metal element other than zirconium is a total amount of the amount of the supported metal and the amount of the metal contained in the zirconium-containing complex metal oxide before the metal is supported.

{Production Method of Metal Supported Type Zirconium-Containing Oxide}

As for the production method of the metal supported type zirconium-containing oxide, the metal supported type zirconium-containing oxide can be, for example, produced by adopting an impregnation method, a CVD method, or a spray drying method.

For example, in the case of the impregnation method, there is exemplified a method in which zirconium oxide and/or the zirconium-containing complex metal oxide as a carrier and the feed raw material of other metal element than zirconium that is a raw material of a substance supported on the carrier are mixed in a solvent and then dried, followed by baking, thereby obtaining the metal supported type zirconium-containing oxide.

Examples of the feed raw material of other metal element than zirconium include a salt of the aforementioned at least one metal element selected from the group consisting of lithium, nickel, copper, zinc, cesium, barium, hafnium, tantalum, cerium, and dysprosium, such as an acetate, a carbonate, a nitrate, a sulfate, and an organic acid salt; a halide, such as a chloride, a bromide, and an iodide; a hydroxide; an alkoxide; and an oxyhalide. The feed raw material may be either an anhydride or a hydrate.

Examples of the solvent which is used for the production of the metal supported type zirconium-containing oxide include water and/or a polar solvent other than water. As the polar solvent, one capable of dissolving the feed raw material of a metal element therein may be used, and examples thereof include an alcohol, such as methanol, ethanol, 1-propanol, 2-propanol, and 1-butanol.

The mixing method of zirconium oxide or the zirconium-containing complex metal oxide, the feed raw material of other metal element than zirconium, and the solvent is not particularly limited and may be performed such that the mixture becomes uniform. Preferably, zirconium oxide or the zirconium-containing complex metal oxide and the feed raw material of other metal element than zirconium are mixed such that the resulting metal supported type zirconium-containing oxide satisfies the aforementioned content of the metal element.

The blending amount of the feed raw material of other metal element than zirconium is preferably 0.01 parts by mass or more, more preferably 0.05 parts by mass or more, still more preferably 0.1 parts by mass or more, yet still more preferably 0.5 parts by mass or more, and even yet still more preferably 0.7 parts by mass or more, and it is preferably 10.0 parts by mass or less, more preferably 7.0 parts by mass or less, still more preferably 5.0 parts by mass or less, yet still more preferably 3.0 parts by mass or less, and even yet still more preferably 1.5 parts by mass or less, as expressed in terms of the metal element other than zirconium based on 100 parts by mass of zirconium in the carrier.

Thereafter, the resulting mixture is, for example, dried under reduced pressure to remove the solvent, and the dried mixture (solid) is baked at a high temperature, whereby the metal supported type zirconium-containing oxide can be obtained.

Though the temperature at the time of baking is not particularly limited, it is preferably 300° C. or higher, more preferably 400° C. or higher, and still more preferably 450° C. or higher, and it is preferably 1,000° C. or lower, more preferably 900° C. or lower, and still more preferably 800° C. or lower.

Though the form on using the zirconium compound is not particularly limited, for example, it may be in a form of powder, particle, or granule, and it may be used as a molded body in a form of sphere, tablet, column, ring, or honeycomb (for example, a molded body obtained through extrusion molding, pressure molding, etc.).

<Water>

While water is used as the solvent of the α-amino acid amide, it is also a reactant for reacting with the α-amino acid amide in the presence of the zirconium compound to hydrolyze the α-amino acid amide.

Though the amount of water to be used in the present invention may be 1 mol or more per mol of the α-amino acid amide, from the viewpoint of improving the yield of the resulting α-amino acid, it is preferably 5 mol or more, more preferably 20 mol or more, and still more preferably 40 mol or more per mol of the α-amino acid amide. Though its upper limit is not particularly limited, from the same viewpoint, the amount of water to be used is preferably 200 mol or less, more preferably 150 mol or less, and still more preferably 100 mol or less per mol of the α-amino acid amide.

<Reaction>

From the viewpoint of improving the yield of the resulting α-amino acid, the reaction temperature on allowing the α-amino acid amide and water to react with each other is preferably 30° C. or higher, more preferably 40° C. or higher, and still more preferably 50° C. or higher, and it is preferably 250° C. or lower, more preferably 220° C. or lower, and still more preferably 200° C. or lower.

In the case where the zirconium compound is the zirconium-containing complex metal oxide, from the viewpoint of improving the yield of the resulting α-amino acid, the reaction temperature is preferably 30° C. or higher, more preferably 40° C. or higher, and still more preferably 50° C. or higher, and it is 250° C. or lower, more preferably 220° C. or lower, and still more preferably 200° C. or lower.

In the case where the zirconium compound is the metal supported type zirconium-containing oxide, from the viewpoint of improving the yield of the resulting α-amino acid, the reaction temperature is preferably 30° C. or higher, more preferably 40° C. or higher, and still more preferably 50° C. or higher, and it is preferably 250° C. or lower, more preferably 220° C. or lower, and still more preferably 200° C. or lower.

The reaction time on allowing the α-amino acid amide and water to react with each other to obtain the α-amino acid varies depending upon the concentration of the α-amino acid amide in the reaction solution, the reaction temperature, the addition amount of the zirconium compound as a catalyst, the reaction mode, etc. Therefore, although the reaction time can be properly regulated, the reaction time is preferably 0.5 hours or more, more preferably 0.7 hours or more, and still more preferably 1.0 hour or more, and it is preferably 5.0 hours or less, more preferably 3.0 hours or less, and still more preferably 2.0 hours or less, for example.

The reaction between the α-amino acid amide and water may be performed under autogenic pressure due to an evaporated or volatized component, such as ammonia generated by the reaction between the α-amino acid amide and water, or the reaction may also be performed while extracting the generated ammonia. In addition, in the case of performing the reaction under temperature conditions exceeding the boiling point of water in the reaction solution, or the like, the reaction may be performed while pressurizing using a pressure vessel, such as an autoclave, as the need arises. The reaction can be properly performed while regulating the pressure within the system at the time of reaction, depending upon the kind of the α-amino acid amide to be used or the resulting α-amino acid, the concentration of the α-amino acid amide in the reaction solution, the reaction temperature, the addition amount of the zirconium compound, etc.

The reaction mode may be either a batchwise method or a continuous method.

For example, in the case of adopting the batchwise method, the use amount of the zirconium compound is preferably 1.0 part by mass or more, more preferably 3.0 parts by mass or more, and still more preferably 5.0 parts by mass or more based on 100 parts by mass of the α-amino acid amide from the viewpoint of improving the yield of the resulting α-amino acid; and it is preferably 200 parts by mass or less, more preferably 100 parts by mass or less, and still more preferably 50.0 parts by mass or less from the viewpoint of inhibiting the side-reaction.

The amount of the zirconium compound is preferably 0.1 parts by mass or more, more preferably 0.4 parts by mass or more, and still more preferably 1.0 part by mass or more based on 100 parts by mass of the total liquid amount of the reaction solution containing the α-amino acid amide and water from the viewpoint of improving the yield of the resulting α-amino acid; and it is preferably 50.0 parts by mass or less, more preferably 30.0 parts by mass or less, and still more preferably 10.0 parts by mass or less from the viewpoint of inhibiting the side-reaction.

In the continuous method, a continuous tank-type reactor and a tubular reactor can be used. The continuous tank-type reactor is also referred to as a continuous stirred tank reactor (CSTR), and by connecting plural reaction tanks in series, the targeted yield can be attained. The tubular reactor is also referred to as a plug flow reactor (PFR), and in order to attain the targeted yield, a packing material can be filled in the reaction tube, or the length of the reaction tube can be altered for the purpose of enhancing the mixing efficiency.

As for the respective reaction conditions in the case of using the CSTR, the reaction can be performed under the same conditions as the aforementioned respective conditions, and suitable ranges thereof are also the same. In addition, in the case of using the PFR, the reaction conditions thereof can be properly set on the basis of the aforementioned respective conditions. In the case of the continuous method, a mean residence time is to be considered as the reaction time.

In the case where the α-amino acid obtained through the reaction between the α-amino acid amide and water is isolated from the reaction solution, the isolation can be achieved by a method, such as filtration, distillation, and crystallization, or a combination of these methods.

EXAMPLES

The present invention is hereunder described in more detail by reference to Examples, but it should be construed that the present invention is by no means limited by these Examples.

[Content of Other Metal Element than Zirconium in Zirconium Compound]

For obtaining the content of other metal element than zirconium in a zirconium compound, a metal other than zirconium is mixed with a zirconium compound prepared under conditions under which the metal other than zirconium was not added and then baked, an increase in weight of the zirconium compound is obtained, and the content of the metal element other than zirconium in the zirconium compound was calculated therefrom.

However, the content of hafnium in "RC-100 Zirconium Oxide" (a product name, manufactured by Daiichi Kigenso Kagaku Kogyo Co., Ltd., hereinafter also referred to simply as "RC-100") that is a zirconium-containing complex oxide was measured by the following method.

Measuring method: Inductively coupled plasma (ICP) emission spectroscopy analysis Analyzer: 720 Series ICP-OES (manufactured by Agilent Technologies)

Analytical wavelength: 263.9 nm

To about 20 mg of "RC-100" weighed in a 50-mL porcelain crucible, 2.5 mL of sulfuric acid (sulfuric acid for measuring toxic metal, manufactured by Kanto Chemical Co., Inc.) and 100 mg of ammonium sulfate (for atomic absorption measurement, manufactured by Junsei Chemical Co., Ltd.) were added to prepare a sample, which was then heated with a hot plate at 300° C. for 2 hours. Furthermore, the resulting sample was heated in an electric furnace to 500° C. and melted. The porcelain crucible after the heat treatment was cooled, and the whole amount was put into a one-liter volumetric flask while washing with water, to make the whole amount to 1,000 mL. The resulting solution was analyzed with the analyzer (ICP-OES), and the content of hafnium contained in RC-100 was calculated.

[Analysis Method of α-Amino Acid Amide and α-Amino Acid]

<Analysis Method of Methionine Amide and Methionine>

For studying the hydrolysis of methionine amide, the analysis by high performance liquid chromatography (HPLC) was performed. The analysis conditions were as follows.

(HPLC Analysis Condition 1)

Column: Shodex (a registered trademark) RSpak NN-814 (manufactured by Showa Denko K.K.)

Column size: 8.0 mm×250 mm

Column temperature: 40° C.

Eluting solution: Aqueous solution in which trifluoroacetic acid was added in a concentration of 0.1% by mass in a mixed solution of acetonitrile/water=50/50 (volume ratio)

Flow rate of eluting solution: 1.2 mL/min

Detector: One in which a UV (ultraviolet ray) 210 nm detector and an RI (refractive index) detector were arranged in series was used.

Under the HPLC Analysis Condition 1, the concentrations of the respective compounds in an analysis solution were calculated by the absolute calibration curve method using standard products that are measuring objects (methionine amide hydrochloride (reagent), manufactured by Wako Pure Chemical Industries, Ltd.; and DL-methionine (reagent), manufactured by Wako Pure Chemical Industries, Ltd.); the methionine amide and methionine concentrations in the reaction solution were calculated; and the conversion (%) of the raw material methionine amide before commencement of the reaction and the yield (%) of methionine were calculated.

<Analysis Method of Glycine Amide and Glycine>

For studying the hydrolysis of glycine amide, the analysis by high performance liquid chromatography (HPLC) was performed. The analysis conditions were as follows.

(HPLC Analysis Condition 2)

Column: Shodex (a registered trademark) RSpak NN-814 (manufactured by Showa Denko K.K.)

Column size: 8.0 mm×250 mm

Column temperature: 40° C.

Eluting solution: 0.1% by mass phosphoric acid aqueous solution containing 8 mM of $KH_2PO_4$ Flow rate of eluting solution: 1.0 mL/min Detector: One in which a UV (ultraviolet ray) 210 nm detector and an RI (refractive index) detector were arranged in series was used.

Under the HPLC Analysis Condition 2, the concentrations of the respective compounds in an analysis solution were calculated by the absolute calibration curve method using standard products that are measuring objects (glycine amide hydrochloride, manufactured by Tokyo Chemical Industry Co., Ltd. or Wako Pure Chemical Industries, Ltd.; and glycine, manufactured by Junsei Chemical Co., Ltd.); the glycine amide and glycine concentrations in the reaction solution were calculated; and the conversion (%) of the raw material glycine amide before commencement of the reaction and the yield (%) of glycine were calculated.

<Analysis Method of Alanine Amide and Alanine>

For studying the hydrolysis of alanine amide, the analysis by high performance liquid chromatography (HPLC) was performed. The analysis was performed under the same conditions as the HPLC Analysis Condition 1 for methionine amide and methionine.

Under the HPLC Analysis Condition 1, the concentrations of the respective compounds in an analysis solution were calculated by the absolute calibration curve method using standard products that are measuring objects (alanine amide hydrochloride, manufactured by Tokyo Chemical Industry Co., Ltd.; and alanine, manufactured by Tokyo Chemical Industry Co., Ltd.); the alanine amide and alanine concentrations in the reaction solution were calculated; and the conversion (%) of raw material alanine amide before commencement of the reaction and the yield (%) of alanine were calculated.

[Preparation of Zirconium Compound]

<Zirconium-Containing Complex Metal Oxide (Hydrothermal Synthesis Product)>

Preparation Example 1

Preparation of Zirconium Compound No. 1

In an inner cylinder tube of a 45-mL hydrothermal synthesis reactor provided with an inner cylinder tube made of polytetrafluoroethylene (PTFE) (manufactured by Parr Instrument Company, a PTFE liner-provided high-temperature high-pressure acid decomposition vessel, vessel size: 45 mL), in which a stirrer was put therein, 0.8 g of zirconium nitrate dihydrate (manufactured by Wako Pure Chemical Industries, Ltd.) and lithium nitrate (manufactured by Kanto Chemical Co., Inc.) in an amount of 10.0 parts by mass, as expressed in terms of lithium, based on 100 parts by mass of zirconium in the zirconium nitrate dihydrate were added and then dissolved in 12.7 mL of water, thereby obtaining a solution.

5.0 g of 28% by mass ammonia water was dropped while stirring the solution. Thereafter, the reactor was closed and heated at 240° C. for 12 hours. Thereafter, the resultant was cooled to room temperature, and the resulting solid was washed with water and filtered, followed by drying at 100° C. for 3 hours. The solid after drying was baked in air at 500° C. for 3 hours to obtain a zirconium-containing complex metal oxide (Zirconium Compound No. 1).

Preparation Examples 2 to 9

Preparation of Zirconium Compounds Nos. 2 to 9

As shown in the following Table 1, Zirconium Compounds Nos. 2 to 9 that are zirconium-containing complex metal oxides were obtained by adopting the same method as in Preparation Example 1, except for changing the feed raw material of other metal element than zirconium to a feed raw material of each of the metal elements as mentioned later.

However, in Preparation Examples 7 and 9, the amount of the feed raw material of other metal element than zirconium was set to 30.0 parts by mass, as expressed in terms of the metal element in the feed raw material of a metal element, based on 100 parts by mass of zirconium in the zirconium dihydrate.

Preparation Example 10

Zirconium Compound No. 10

"RC-100 Zirconium Oxide" (a product name, manufactured by Daiichi Kigenso Kagaku Kogyo Co., Ltd., content of hafnium based on 100 parts by weight of zirconium: 1.0 part by mass) that is a zirconium-containing complex oxide was used as Zirconium Compound No. 10.

Preparation Examples 101 to 103

Preparation of Zirconium Compounds Nos. 101 to 103

Zirconium Compounds Nos. 101 to 103 that are zirconium-containing complex metal oxides were obtained by adopting the same method as in Preparation Example 1, except for changing the feed raw material of other metal element than zirconium to a feed raw material of each of the metal elements as mentioned later so as to have the content of the metal element other than zirconium as shown in the following Table 3.

Preparation Example 104

Zirconium Compound No. 104

Zirconium Compound No. 104 that is zirconium oxide was obtained by adopting the same method as in Preparation Example 1, except that in Preparation Example 1, the compound serving as the raw material of other metal element than zirconium was not added.

Feed raw materials of other metal element than zirconium as used in Preparation Examples 1 to 9 and 101 to 103 are shown below.

Lithium (Li): "Lithium nitrate" (manufactured by Kanto Chemical Co., Inc.)

Tantalum (Ta): "Tantalum(V) chloride" (manufactured by Wako Pure Chemical Industries, Ltd.)

Copper (Cu): "Copper(II) nitrate trihydrate" (manufactured by Wako Pure Chemical Industries, Ltd.)

Hafnium (Hf): "Hafnium(IV) sulfate" (manufactured by Sigma-Aldrich)

Cerium (Ce): "Cerium(III) nitrate hexahydrate" (manufactured by Wako Pure Chemical Industries, Ltd.)

Zinc (Zn): "Zinc nitrate hexahydrate" (manufactured by Wako Pure Chemical Industries, Ltd.)

Nickel (Ni): "Nickel(II) nitrate hexahydrate" (manufactured by Junsei Chemical Co., Ltd.)

Iron (Fe): "Iron(III) nitrate nonahydrate" (manufactured by Junsei Chemical Co., Ltd.)

Yttrium (Y): "Yttrium(III) nitrate hexahydrate" (manufactured by Junsei Chemical Co., Ltd.)

Titanium (Ti): "Titanium(IV) tetrabutoxide, monomer" (manufactured by Wako Pure Chemical Industries, Ltd.)

<Metal Supported Type Zirconium-Containing Oxide>

Preparation Example 11

Preparation of Zirconium Compound No. 11

In a glove box in a nitrogen atmosphere, the whole amount of a solution of 0.0074 g of lithium nitrate (manufactured by Kanto Chemical Co., Inc.) dissolved in 0.88 g of water was gradually dropped in 1.0 g of "RC-100 Zirconium Oxide" (a product name, manufactured by Daiichi Kigenso Kagaku Kogyo Co., Ltd., content of hafnium based on 100 parts by weight of zirconium:1.0 part by mass) that is a zirconium-containing complex oxide, as charged in a 9-mL vial made of a Pyrex (a registered trademark) glass while mixing with a spatula. A uniformly mixed mixture was charged in a heating type vacuum dryer and dried at 50° C. for 1 hour under reduced pressure conditions, thereby removing the moisture. A solid after drying was transferred into a crucible and baked in air at 500° C. for 3 hours, thereby obtaining a metal supported type zirconium-containing oxide (Zirconium Compound No. 11).

Preparation Examples 12 to 18

Preparation of Zirconium Compounds Nos. 12 to 18

Zirconium Compounds Nos. 12 to 17 that are metal supported type zirconium-containing oxides were obtained by adopting the same method as in Preparation Example 11, except for changing the feed raw material of other metal element than zirconium to a feed raw material of each of the metal elements as mentioned later so as to have the content of the metal element other than zirconium as shown in the following Table 2.

Furthermore, Zirconium Compound No. 18 was obtained by adopting the same method as in Preparation Example 11, except for not only changing the feed raw material of other metal element than zirconium to "zinc nitrate hexahydrate" (manufactured by Wako Pure Chemical Industries, Ltd.) as mentioned later so as to have the content of the zinc as shown in the following Table 2 but also changing the carrier from the "RC-100 Zirconium Oxide" to the "Zirconium Compound No. 104".

Feed raw materials of other metal element than zirconium as used in Preparation Examples 11 to 18 are shown below.

Lithium (Li): "Lithium nitrate" (manufactured by Kanto Chemical Co., Inc.)

Dysprosium (Dy): "Dysprosium nitrate pentahydrate" (manufactured by Kanto Chemical Co., Inc.)

Cesium (Cs): "Cesium nitrate" (manufactured by Wako Pure Chemical Industries, Ltd.)

Barium (Ba): "Barium nitrate" (manufactured by Kanto Chemical Co., Inc.)

Zinc (Zn): "Zinc nitrate hexahydrate" (manufactured by Wako Pure Chemical Industries, Ltd.)

[Production of α-Amino Acid]
<Synthesis of Raw Material Substrate>

Synthesis of 2-[2-(Methylthio)ethyl]-2-aminoacetonitrile

Synthesis Example 1

Into a one-liter flask heated at 40° C. in a water bath, 7.2 g of a 70% by mass hydrogen cyanide aqueous solution, 103.5 g of a 28% by mass saturated ammonia aqueous solution (manufactured by Wako Pure Chemical Industries, Ltd.), and 18.3 g of methylmercapto propionaldehyde (manufactured by Sigma-Aldrich) were fed while stirring with a stirrer such that the whole amount was completely transferred within 1 hour.

After completion of feed, the resultant was further aged for 30 minutes, thereby preparing a reaction solution containing 2-[2-(methylthio)ethyl]-2-aminoacetonitrile.

A part of the reaction solution was taken out and analyzed under the HPLC Analysis Condition 1, thereby confirming the concentration of 2-[2-(methylthio)ethyl]-2-aminoacetonitrile in the reaction solution. As a result, the concentration in the reaction solution was found to be 16.1% by mass.

Synthesis of Methionine Amide (the Same as "2-amino-4-(methylthio)butanamide")

Synthesis Example 2

In a 2-L flask in a water bath at 20° C., 257.1 g of an aqueous solution containing 2-[2-(methylthio)ethyl]-2-aminoacetonitrile as synthesized in the method of Synthesis Example 1 in a concentration of 16.1% by mass was added, and 153.3 g of water, 53.66 g of acetone (manufactured by Junsei Chemical Co., Ltd.), and 3.09 g of 20% by mass NaOH (solution in which solid NaOH, manufactured by Junsei Chemical Co., Ltd., was dissolved in pure water to an extent of 20% by mass) were then added at room temperature while stirring with a stirrer.

After completion of addition, the resultant was kept at a temperature of 20° C. in a water bath and aged for 3 hours, thereby preparing a reaction solution of methionine amide.

A part of the reaction solution was taken out and analyzed under the HPLC Analysis Condition 1, thereby confirming the concentration of methionine amide in the reaction solution. As a result, the concentration in the reaction solution was found to be 10.5% by mass.

<Synthesis of α-Amino Acid>
(Production of Methionine)

Example 1

The reaction solution containing methionine amide as synthesized in the method of Synthesis Example 2 was treated under reduced pressure, thereby distilling off the ammonia and acetone. Water was added to the liquid after distillation, thereby preparing an aqueous solution of methionine amide in a concentration of 11.0% by mass.

In a 30-mL stainless steel-made pressure vessel having a stirrer put thereinto, 0.1 g of Zirconium Compound No. 1 as synthesized according to the method of Preparation Example 1 and 10.0 g of the aqueous solution of methionine amide in a concentration of 11.0% by mass were added, and the reactor was then hermetically closed to perform the reaction at 130° C. for 1.0 hour while stirring. Thereafter, the reaction solution was cooled to room temperature. As a result of HPLC analysis of the reaction solution within the reactor, the conversion of methionine amide was 100%, and the yield of methionine on the basis of methionine amide was 98.2%.

Examples 2 to 21

The hydrolysis of methionine amide was performed by adopting the same method as in Example 1, except that as shown in the following Tables 1 and 2, each of Zirconium Compounds Nos. 2 to 18 was used as the zirconium compound, and that the reaction conditions were changed. The obtained results are shown in Tables 1 and 2.

Comparative Examples 1 to 4

The hydrolysis of methionine amide was performed by adopting the same method as in Example 1, except that each of Zirconium Compounds Nos. 101 to 104 was used as the zirconium compound. The obtained results are shown in Table 3.

Comparative Example 5

The hydrolysis of methionine amide was performed by adopting the same method as in Example 1, except that the zirconium compound was changed to zinc hydroxide (manufactured by Junsei Chemical Co., Ltd.). The obtained results are shown in Table 3.

Comparative Example 6

The hydrolysis of methionine amide was performed by adopting the same method as in Example 1, except that the zirconium compound was changed to titanium oxide (anatase type, manufactured by Junsei Chemical Co., Ltd.). The obtained results are shown in Table 3.

Comparative Example 7

The hydrolysis of methionine amide was performed by adopting the same method as in Example 1, except that the hydrolysis reaction was performed without using a catalyst. The obtained results are shown in Table 3.

(Production of Other α-Amino Acid)

Example 22

Glycine amide hydrochloride was dissolved in water in an amount at which the concentration of glycine amide in liquid was 7.5% by mass, and the solution was neutralized upon addition of sodium hydroxide in the same molar amount as the glycine amide hydrochloride, thereby preparing an aqueous solution of free glycine amide.

In a 15-mL glass-made pressure vessel having a stirrer put thereinto, 10.0 g of the aqueous solution of glycine amide in a concentration of 7.5% by mass and 0.1 g of Zirconium Compound No. 16 as the zirconium compound were added, and the reactor was then hermetically closed to perform the reaction at 130° C. for 1.0 hour while stirring. Thereafter, the reaction solution was cooled to room temperature, and the reaction solution within the reactor was subjected to HPLC analysis. As a result, the conversion of glycine amide was 100%, and the yield of glycine on the basis of glycine amide was 94.5%.

Example 23

The hydrolysis of alanine amide was performed in the same method as in Example 22 by using Zirconium Compound No. 16 as the zirconium compound, thereby obtaining alanine. The obtained results are shown in Table 4.

Example 24

The hydrolysis of glycine amide was performed in the same method as in Example 22 by using Zirconium Compound No. 10 as the zirconium compound, thereby obtaining glycine. The obtained results are shown in Table 4.

TABLE 1

| | Zirconium compound | | | Reaction conditions | | | | Results | |
|---|---|---|---|---|---|---|---|---|---|
| | | Other metal element than zirconium | | Use amount of zirconium | Concentration of raw | Reaction | Reaction | Conversion of | Yield of |
| | No. | Kind | Content *1 (parts by mass) | compound *2 (parts by mass) | material *3 (mass %) | temperature (° C.) | time (hr) | methionine amide (%) | methionine (%) |
| Example 1 | 1 | Li | 0.1 | 1.0 | 11.0 | 130 | 1.0 | 100 | 98.2 |
| Example 2 | 2 | Ta | 9.6 | 1.0 | 11.0 | 130 | 1.0 | 99.2 | 98.2 |
| Example 3 | 3 | Cu | 4.5 | 1.0 | 11.0 | 130 | 1.0 | 100 | 97.6 |
| Example 4 | 4 | Hf | 10.0 | 1.0 | 11.0 | 130 | 1.0 | 100 | 97.4 |
| Example 5 | 5 | Ce | 8.9 | 1.0 | 11.0 | 130 | 1.0 | 92.7 | 92.3 |
| Example 6 | 6 | Zn | 4.3 | 1.0 | 11.0 | 130 | 1.0 | 100 | 99.7 |
| Example 7 | 7 | Zn | 6.1 | 1.0 | 11.0 | 130 | 1.0 | 96.7 | 96.4 |
| Example 8 | 8 | Ni | 3.6 | 1.0 | 11.0 | 130 | 1.0 | 100 | 99.1 |
| Example 9 | 9 | Ni | 11.4 | 1.0 | 11.0 | 130 | 1.0 | 100 | 100 |
| Example 10 | 10 | Hf | 1.0 | 1.0 | 11.0 | 130 | 1.0 | 98.3 | 89.8 |

*1: Content of other metal element than zirconium based on 100 parts by mass of zirconium in zirconium compound.
*2: Concentration of zirconium compound based on 100 parts by mass of the whole liquid amount (exclusive of solids) in reaction solution.
*3: Concentration of raw material (methionine amide) in reaction solution (exclusive of solids).

TABLE 2

| | Zirconium compound | | | Reaction conditions | | | | Results | |
|---|---|---|---|---|---|---|---|---|---|
| | | Supporting metal element | | Use amount of zirconium | Concentration of raw | Reaction | Reaction | Conversion of | Yield of |
| | No. | Kind | Content *4 (parts by mass) | compound *2 (parts by mass) | material *3 (mass %) | temperature (° C.) | time (hr) | methionine amide (%) | methionine (%) |
| Example 11 | 11 *5 | Li | 0.1 | 1.0 | 10.0 | 90 | 1.0 | 96.9 | 94.9 |
| Example 12 | 12 *5 | Dy | 0.1 | 1.0 | 10.0 | 90 | 1.0 | 95 | 95.5 |

TABLE 2-continued

| | Zirconium compound | | | Reaction conditions | | | | Results | |
|---|---|---|---|---|---|---|---|---|---|
| | | Supporting metal element | | Use amount of zirconium | Concentration of raw | Reaction | Reaction | Conversion of | Yield of |
| | No. | Kind | Content *4 (parts by mass) | compound *2 (parts by mass) | material *3 (mass %) | temperature (° C.) | time (hr) | methionine amide (%) | methionine (%) |
| Example 13 | 13 *5 | Cs | 0.1 | 1.0 | 10.0 | 90 | 1.0 | 93.3 | 90.8 |
| Example 14 | 14 *5 | Ba | 0.5 | 1.0 | 10.0 | 90 | 1.0 | 92.3 | 90.0 |
| Example 15 | 15 *5 | Zn | 0.1 | 1.0 | 10.0 | 90 | 1.0 | 96.8 | 95.4 |
| Example 16 | 16 *5 | Zn | 1.0 | 1.0 | 10.0 | 90 | 1.0 | 100 | 97.7 |
| Example 17 | 17 *5 | Zn | 2.0 | 1.0 | 10.0 | 90 | 1.0 | 96.3 | 93.8 |
| Example 18 | 16 *5 | Zn | 1.0 | 1.0 | 11.0 | 130 | 1.0 | 100 | 99.6 |
| Example 19 | 16 *5 | Zn | 1.0 | 1.0 | 11.0 | 180 | 1.0 | 100 | 96.8 |
| Example 20 | 18 *6 | Zn | 1.0 | 1.0 | 11.0 | 130 | 1.0 | 98.7 | 95.7 |
| Example 21 | 18 *6 | Zn | 1.0 | 1.0 | 11.0 | 180 | 1.0 | 99.3 | 99.3 |

*2: Concentration of zirconium compound based on 100 parts by mass of the whole liquid amount (exclusive of solids) in reaction solution.
*3: Concentration of raw material (methionine amide) in reaction solution (exclusive of solids).
*4: Content (supporting amount) of other metal element than zirconium based on 100 parts by mass of zirconium in zirconium compound; however, content of metal exclusive of Hf derived from RC-100.
*5: Supported on "RC-100 Zirconium Oxide".
*6: Supported on Zirconium Compound No. 104.

TABLE 3

| | Zirconium compound or other catalyst | | | Reaction conditions | | | | Results | |
|---|---|---|---|---|---|---|---|---|---|
| | | Other metal element than zirconium | | Amount of | Concentration of raw | Reaction | Reaction | Conversion of | Yield of |
| | No. | Kind | Content *1 (parts by mass) | catalyst *2 (parts by mass) | material *3 (mass %) | temperature (° C.) | time (hr) | methionine amide (%) | methionine (%) |
| Comparative Example 1 | 101 | Fe | 9.9 | 1.0 | 11.0 | 130 | 1.0 | 86.9 | 86.1 |
| Comparative Example 2 | 102 | Y | 9.9 | 1.0 | 11.0 | 130 | 1.0 | 87.1 | 83.1 |
| Comparative Example 3 | 103 | Ti | 10.0 | 1.0 | 11.0 | 130 | 1.0 | 70.8 | 70.2 |
| Comparative Example 4 | 104 | — | — | 1.0 | 11.0 | 130 | 1.0 | 100 | 86.9 |
| Comparative Example 5 | Zn(OH)$_2$ | — | — | 1.0 | 11.0 | 130 | 1.0 | 25.2 | 12.1 |
| Comparative Example 6 | TiO$_2$ | — | — | 1.0 | 11.0 | 130 | 1.0 | 21.7 | 16.6 |
| Comparative Example 7 | Not using catalyst | — | — | — | 11.0 | 130 | 1.0 | 8.1 | 6.7 |

*1: Content of other metal element than zirconium based on 100 parts by mass of zirconium in zirconium compound.
*2: Concentration of zirconium compound or other catalyst based on 100 parts by mass of the whole liquid amount (exclusive of solids) in reaction solution.
*3: Concentration of raw material (methionine amide) in reaction solution (exclusive of solids).

TABLE 4

| | Zirconium compound | | | Reaction conditions | | | | Results | | |
|---|---|---|---|---|---|---|---|---|---|---|
| | | Other metal element than zirconium | | Use amount of zirconium | Concentration of raw | Reaction temper- | Reaction | Conversion of α-amino | Yield of α-amino | α-Amino |
| | No. | Kind | Content (parts by mass) | compound *2 (parts by mass) | material *3 (mass %) | ature (° C.) | time (hr) | acid amide (%) | acid (%) | acid |
| Example 22 | 16 *5 | Zn | 1.0 *4 | 1.0 | 7.5 | 130 | 1.0 | 100 | 94.5 | Glycine |
| Example 23 | 16 *5 | Zn | 1.0 *4 | 1.0 | 8.9 | 130 | 1.0 | 100 | 88.6 | Alanine |
| Example 24 | 10 | Hf | 1.0 | 1.0 | 7.5 | 130 | 1.0 | 100 | 86.9 | Glycine |

*2: Concentration of zirconium compound based on 100 parts by mass of the whole liquid amount (exclusive of solids) in reaction solution.
*3: Concentration of raw material (α-amino acid) in reaction solution (exclusive of solids).
*4: Content (supporting amount) of other metal element than zirconium based on 100 parts by mass of zirconium in zirconium compound; however, content of metal exclusive of Hf derived from RC-100.
*5: Supported on "RC-100 Zirconium Oxide".

[Results]

As shown in Tables 1 to 3, from comparison of Examples 1 to 21 with Comparative Examples 1 to 7, it was confirmed that by using the zirconium compounds described in Examples 1 to 21, methionine is obtained in a higher yield.

On the other hand, in Comparative Examples 1 to 3, since the specified element is not contained as the metal element other than zirconium, the yields of methionine turned out to be inferior to that in each of the Examples. In addition, in Comparative Example 4, since only a simple substance of zirconium oxide is used, the yield of methionine turned out to be inferior to that in each of the Examples. In addition, in Comparative Examples 5 and 6, since zinc hydroxide and titanium oxide are each independently used in place of the zirconium compound, and the zirconium compound is not used as the catalyst, the yields of methionine turned out to be inferior to that in each of the Examples. In addition, in Comparative Example 7, since the hydrolysis is performed without using a catalyst, the yield of methionine turned out to be inferior to that in each of the Examples.

Furthermore, as shown in Examples 22 to 24 in Table 4, it is confirmed that the production method of the present invention is effective not only in a case of producing methionine, but also in a case of producing glycine and alanine.

INDUSTRIAL APPLICABILITY

By adopting the production method of an α-amino acid of the present invention, the α-amino acid can be obtained simply and easily through hydrolysis of an α-amino acid amide. Furthermore, since it is possible to improve the yield of the α-amino acid as compared with the conventional production method, the production method of an α-amino acid of the present invention is suitable as the production method for obtaining an α-amino acid from an α-amino acid amide.

The invention claimed is:

1. A method for producing an α-amino acid represented by the following general formula (2), comprising reacting an α-amino acid amide represented by the following general formula (1) with water in the presence of a zirconium compound which contains zirconium and at least one metal element selected from the group consisting of lithium, nickel, copper, zinc, cesium, barium, hafnium, tantalum, cerium, and dysprosium:

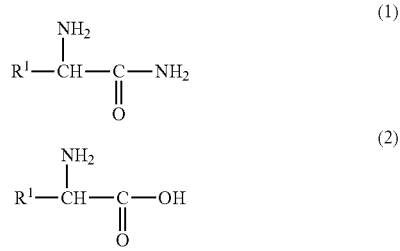

wherein
in the general formulae (1) and (2), $R^1$ is a hydrogen atom, an optionally substituted alkyl group having 1 to 6 carbon atoms, an optionally substituted cycloalkyl group having 3 to 6 carbon atoms, an optionally substituted aryl group having a ring-constituting carbon number of 6 to 10, or an optionally substituted heteroaryl group having a ring-constituting atom number of 4 to 13.

2. The method for producing an α-amino acid according to claim 1, wherein the zirconium compound is a zirconium-containing oxide.

3. The method for producing an α-amino acid according to claim 2, wherein the zirconium-containing oxide comprises a complex metal oxide containing zirconium and at least one metal element selected from the group consisting of lithium, nickel, copper, zinc, cesium, barium, hafnium, tantalum, cerium, and dysprosium.

4. The method for producing an α-amino acid according to claim 3, wherein the zirconium-containing oxide comprises a supported type metal oxide in which a metal compound containing at least one metal element selected from the group consisting of lithium, nickel, copper, zinc, cesium, barium, hafnium, tantalum, cerium, and dysprosium is supported on (i) zirconium oxide or (ii) the complex metal oxide.

5. The method for producing an α-amino acid according to claim 3, wherein the content of the metal element other than zirconium in the complex metal oxide is 0.01 parts by mass or more and 100 parts by mass or less based on 100 parts by mass of zirconium.

6. The method for producing an α-amino acid according to claim 4, wherein the amount of the at least one metal element selected from the group consisting of lithium, nickel, copper, zinc, cesium, barium, hafnium, tantalum, cerium, and dysprosium that is supported in the supported type metal oxide is 0.01 parts by mass or more and 10.0 parts by mass or less based on 100 parts by mass of zirconium.

7. The method for producing an α-amino acid according to claim 1, wherein the zirconium compound is used in an amount of 1.0 part by mass or more and 200 parts by mass or less based on 100 parts by mass of the α-amino acid amide.

8. The method for producing an α-amino acid according to claim 1, wherein the α-amino acid amide is glycine amide, alanine amide, or methionine amide.

9. The method for producing an α-amino acid according to claim 2, wherein the zirconium-containing oxide is a supported type metal oxide in which a metal compound containing at least one metal element selected from the group consisting of lithium, nickel, copper, zinc, cesium, barium, hafnium, tantalum, cerium, and dysprosium is supported on zirconium oxide.

10. The method for producing an α-amino acid according to claim 9, wherein the amount of the at least one metal element selected from the group consisting of lithium, nickel, copper, zinc, cesium, barium, hafnium, tantalum, cerium, and dysprosium that is supported in the supported type metal oxide is 0.01 parts by mass or more and 10.0 parts by mass or less based on 100 parts by mass of zirconium.

11. The method for producing an α-amino acid according to claim 1, wherein the zirconium compound contains zirconium and at least one metal element selected from the group consisting of lithium, nickel, copper, zinc, cesium, barium, hafnium, tantalum, and dysprosium.

12. The method for producing an α-amino acid according to claim 1, wherein the zirconium compound is used in an amount of 1.0 part by mass or more and 50.0 parts by mass or less based on 100 parts by mass of the α-amino acid amide.

* * * * *